United States Patent
Ritter, III et al.

(10) Patent No.: US 9,402,781 B2
(45) Date of Patent: Aug. 2, 2016

(54) MANOMETER WITH CADENCE INDICATOR

(71) Applicant: MERCURY ENTERPRISES, INC., Clearwater, FL (US)

(72) Inventors: James Russell Ritter, III, Largo, FL (US); Jeffrey B. Ratner, Pinellas Park, FL (US); Frank Pecoraro, Oceanside, CA (US)

(73) Assignee: MERCURY ENTERPRISES, INC., Clearwater, FL (US)

( * ) Notice: Subject to any disclaimer, the term of this patent is extended or adjusted under 35 U.S.C. 154(b) by 243 days.

(21) Appl. No.: 14/296,548

(22) Filed: Jun. 5, 2014

(65) Prior Publication Data

US 2015/0352001 A1    Dec. 10, 2015

(51) Int. Cl.
*G01L 7/04*    (2006.01)
*A61H 31/00*   (2006.01)
*G01L 13/02*   (2006.01)
*G01L 7/16*    (2006.01)
*A61N 1/39*    (2006.01)

(52) U.S. Cl.
CPC ............ *A61H 31/005* (2013.01); *A61N 1/3987* (2013.01); *G01L 7/166* (2013.01); *G01L 13/026* (2013.01)

(58) Field of Classification Search
None
See application file for complete search history.

(56) References Cited

U.S. PATENT DOCUMENTS

| | | | | | |
|---|---|---|---|---|---|
| 3,908,129 | A | * | 9/1975 | Akers | G01F 23/292 250/341.1 |
| 4,872,483 | A | * | 10/1989 | Shah | A61M 16/044 128/207.15 |
| 5,138,886 | A | * | 8/1992 | Tilley, Sr. | G01L 13/04 73/304 R |
| D748,773 | S | * | 2/2016 | Ritter, III | D10/83 |
| 2003/0192547 | A1 | * | 10/2003 | Lurie | A61H 31/005 128/207.12 |
| 2006/0173501 | A1 | * | 8/2006 | Stickney | A61B 5/046 607/5 |
| 2009/0024175 | A1 | * | 1/2009 | Freeman | A61H 31/00 607/6 |
| 2011/0296928 | A1 | * | 12/2011 | Cheng | G01L 27/007 73/749 |
| 2012/0302910 | A1 | * | 11/2012 | Freeman | A61M 16/0084 600/538 |
| 2013/0030316 | A1 | * | 1/2013 | Popov | A61B 5/01 600/543 |
| 2013/0310718 | A1 | * | 11/2013 | Jensen | A61H 31/005 601/41 |
| 2015/0257971 | A1 | * | 9/2015 | Chapman | A61H 31/005 601/21 |

* cited by examiner

*Primary Examiner* — Andre Allen
(74) *Attorney, Agent, or Firm* — Larson & Larson, P.A.; Frank Liebenow; Justin P. Miller

(57) ABSTRACT

A manometer with a cadence indicator includes a housing and a gas pressure indicator interfaced to the housing. An input port of the housing is for connecting the manometer to a source of gas pressure, such that the gas pressure at the input port is reflected in the gas pressure indicator, providing a pressure reading. A cadence module is interfaced to the housing such that cadence is provided concurrently from the local of the gas pressure indicator. Cadence is provided by a flashing light or audible noise.

15 Claims, 3 Drawing Sheets

MANOMETER WITH CADENCE INDICATOR

CROSS-REFERENCE TO RELATED APPLICATION

This application is related to U.S. patent application Ser. No. 29/493,024, filed even date here within on Jun. 5, 2014.

FIELD

This invention relates to the field of medicine and more particularly to a system for measuring breath pressure while concurrently and locally marking cadence.

BACKGROUND

Often, when performing various procedures on a patient (for example cardio-pulmonary resuscitation or CPR), it is beneficial to know the air pressure that is being used to inflate the patient's lungs and/or exhaled by the patient if the patient is breathing. Likewise, in many procedures, it is beneficial to keep a specific cadence such as 100 times per minute for providing chest compressions during CPR. Also, when resuscitating an adult, it is often beneficial to deliver one breath every 6 seconds, or 10 breaths per minute.

Some systems such as defibrillators provide an audible or visible metronome for compression frequency, but with such, the caretaker must look away from the patient and towards the defibrillators to see such metronomes.

What is needed is a system that will include both breathing pressure and cadence in view of a caretaker while performing procedures upon a patient.

SUMMARY

A manometer is used in many medical procedures to measure and display pressure of a gas, typically air, oxygen, or a mix of oxygen and other gases provided to initiate or assist with breathing by a patient such as when cardio pulmonary resuscitation (CPR) is performed on the patient. Often, a provider (e.g. a person administering CPR) uses the displayed pressure to achieve a proper pressure for the specific patient as to properly inflate the patient's lungs without over-inflating. In many such medical procedures, it is also necessary to maintain a specific cadence, for example when making chest compressions during CPR. Although there are often periodically changes to the suggested cadence, current CPR guidelines indicate a preferred chest compression rate of 100 compressions per minute and 10 breaths per minute. The manometer disclosed includes a cadence device (e.g. pulses of light or pulses of sound) to provide a proper cadence for the intended use, such as 100 blinks/tones per minute for use in administration of chest compressions or 10 blinks/tones per minute for use in delivering breaths to the patient. By integrating the manometer and cadence device, the person performing CPR need not constantly change eye focus between the manometer and cadence device while, for example, saving a person's life. In past systems, a cadence device was on, for example, a defibrillator or was a stand-alone device, adding to confusion during an emergency (e.g. finding separate components) and forcing the provider to look back and forth between the manometer and the distant cadence device.

In one embodiment, a manometer with a cadence indicator is disclosed including a housing and a gas pressure indicator interfaced to the housing. An input port is provided for connecting the manometer to a source of gas pressure, such that the gas pressure at the input port is reflected in the gas pressure indicator, providing a pressure reading. A cadence module is interfaced to the housing such that cadence is provided concurrently from the local of the gas pressure indicator. Cadence is provided by a flashing light or audible noise.

In another embodiment, a method of performing CPR is disclosed including periodically pressurizing a patients lungs while measuring pressure through a manometer and applying chest compressions at a rate determined by a cadence device, the cadence device providing pulses at a rate of approximately 100 pulses per minute. The manometer and the cadence device are integrated with a common housing.

In another embodiment, a manometer with a cadence indicator is disclosed including a housing and a hub with pointer rotatably interfaced within the housing. The hub is biased by a resilient member such that at atmospheric pressure, the pointer indicates a zero reading on a set of gas pressure indicia. An input port for connecting the manometer to a source of gas pressure provides the gas pressure to a diaphragm such that increases in the gas pressure above atmospheric pressure works against the bias of the resilient member, therefore rotating the hub such that the pointer addresses a corresponding indicia related to the pressure on the gas pressure indicia. The manometer with a cadence indicator includes a cadence module interfaced to the housing such that cadence (visible or audible) is provided concurrently from the local of the gas pressure indicia.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
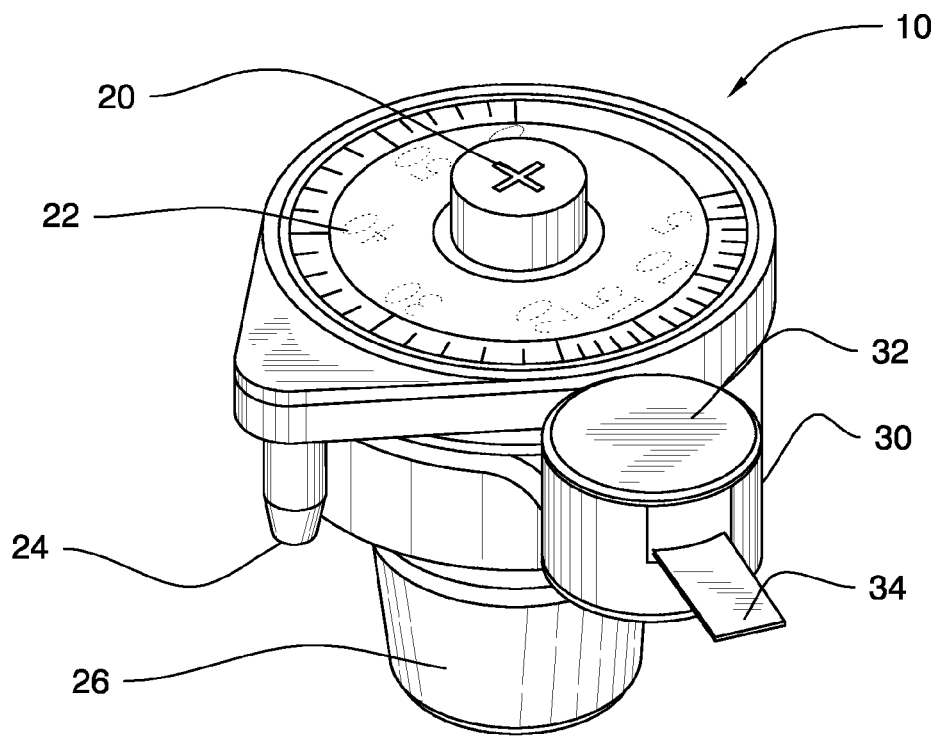
FIG. 1 illustrates a perspective view of a manometer with a cadence indicator.

Reference will now be made in detail to the presently preferred embodiments of the invention, examples of which are illustrated in the accompanying drawings. Throughout the following detailed description, the same reference numerals refer to the same elements in all figures.

Although useful in many applications, one known use for the manometer with attached cadence device 10 is when performing cardio-pulmonary resuscitation. In such, a practitioner often uses an inflation device such as a CPR bag to inflate the patient's lungs while/between chest compressions. In such procedures, it is often desired to maintain a chest compression rate of 100 compressions per minute and/or administering of 10 breaths per minute. Additionally, depending upon the patient's age and/or body mass, specific lung filling pressures are desired so as to not underinflate or over-inflate/rupture the patient's lungs. Therefore, in this application, the manometer with attached cadence device 10, attached to the CPR bag, provides a visual or audible cadence of, for example, approximately 10 per minute and concurrently displays the air pressure being introduced into the patient's lungs at the display 20/22 of the manometer section.

Figure 2:
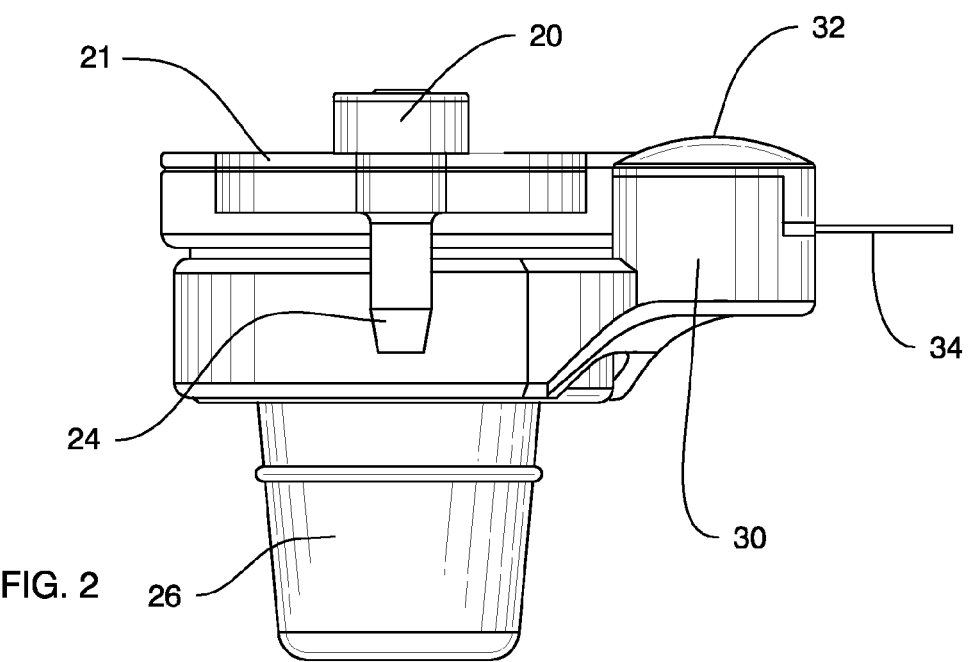
FIG. 2 illustrates a side view of a manometer with a cadence indicator.

Referring to FIGS. 1 and 2, views of an exemplary manometer with attached cadence device 10 are shown. The manometer portion is housed within an enclosure, typically made of plastic, and includes a hub 20 around which a dial rotates, pointing to successive indicators 22, indicating a gas pressure measurement of a pressure entering the manometer through an input port 24. Although any type and composition of manometer is equally anticipated, one such manometer includes a base section 26 that houses a spring or other resilient member that counteracts the gas pressure as the gas pressure is exerted against, for example, a diaphragm. U.S. Pat. No. 5,557,049, issued Sep. 17, 1996 and included by reference, discloses one exemplary manometer, showing one way to construct/build a manometer as an example and any similar or different construction is fully anticipated. Any type of manometer, analog or digital, is anticipated, as long as responsive to pressurized gas entering the manometer inlet 24, the indicator (either analog or digital) on the manometer provides an indication of the pressure of such gas. In the example of U.S. Pat. No. 5,557,049, a diaphragm reciprocates against the force of a biasing spring moving the stem coupling with respect to the actuator stem for the pointer so that the interaction between the spiral-shaped protrusion and the groove causes rotation of the pointer to indicate the pressure of the gas. Such manometers are intended to be used with a CPR bag or a patient breathing tube, though there is no restriction on the use of the present invention. In FIG. 2, a clear cover 21 is visible, covering the dial and indicators 22 to, for example, contain system pressure and prevent debris from interfering with the movement of the dial.

Included in the manometer with attached cadence device 10 is a cadence module 30/32/34. In some embodiments, the cadence module 30/32/34 includes an internal circuit 70 (see FIGS. 3 and 4) that generates pulses at a fixed interval and an indicator 32 (e.g. an LED) or a transducer 84 (e.g. speaker), thereby emitting light pulses or sound responsive to the pulses from the electronic circuit 70. The circuit 70 and indicator 32 or transducer 84 are typically powered by one or more battery cells 62 (see FIGS. 3 and 4). In some embodiments, though not required, a switch or interrupter 34 is provided to disconnect the battery cell(s) from the circuit until needed, thereby preserving battery power until the cadence module 30/32/34 is needed. As shown, the switch or interrupter 34 is a pull strip 34 made of an electrically insulative material (e.g. plastic, Teflon, etc.) and is positioned electrically between the battery(s) and the circuit 70 during manufacturing, thereby disconnecting the battery(s) from the circuit 70 until the pull strip 34 is pulled/removed, at which time the battery(s) are connected to the circuit 70 and the cadence module 30/32/34 starts operation.

In an alternate embodiment, instead of a visual indicator 32, the circuit 70 is connected to an audio transducer 84 (see FIG. 4) and each pulse from the circuit 70 generates a sound at the audio transducer 84.

Figure 3:
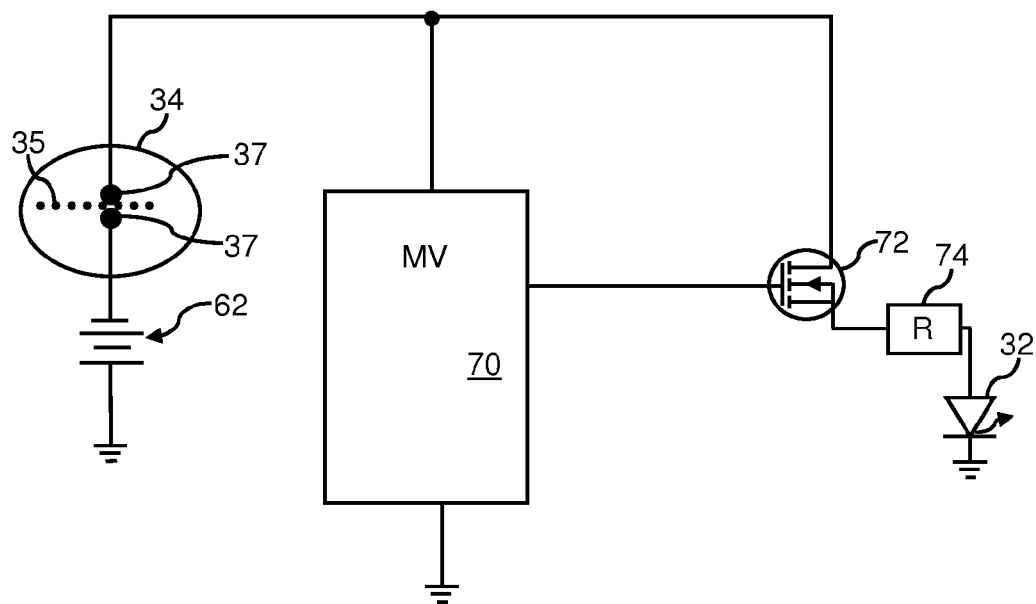
FIG. 3 illustrates an exemplary schematic view of a visual metronome.
Figure 4:
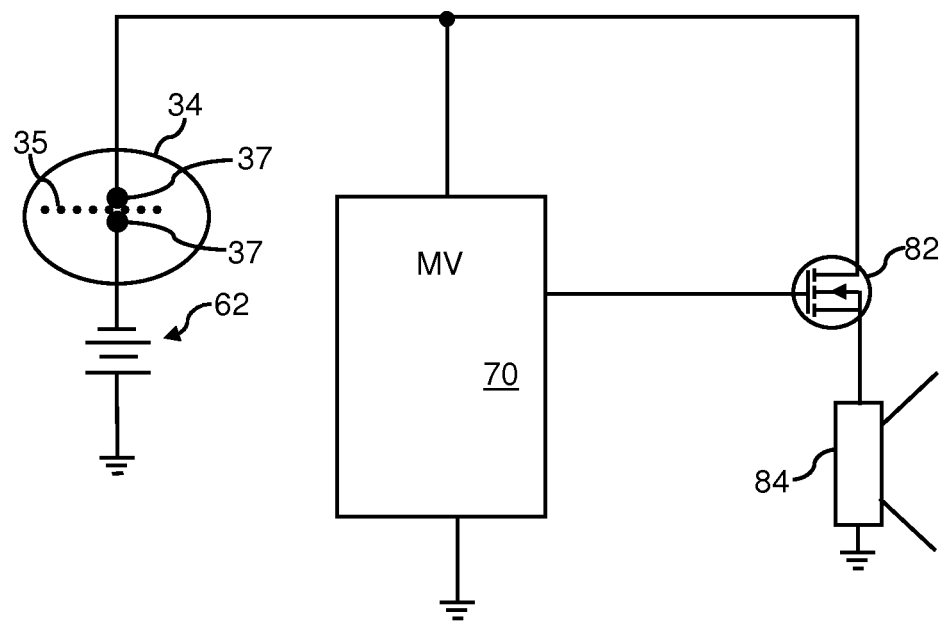
FIG. 4 illustrates an exemplary schematic view of an audio metronome.

Referring to FIGS. 3 and 4, exemplary schematic views of a visual metronome (FIG. 3) and an audio metronome (FIG. 4) are shown. Both exemplary metronomes provide a cadence beat as used in the specific application of the manometer with attached cadence device 10. In both examples, a switch 34 is shown with an insulator 35 inserted between contacts 37, thereby disconnecting the battery 62 from the other circuitry of the cadence module. Once the insulator 35 is extracted from between the contacts 37, power is supplied to the pulse generator circuit 70 and, in the visual metronome of FIG. 3, to a driver 72 that provides power pulses to the indicator 32 (e.g. LED), typically though a current limiting resistor 74. Note that in some embodiments, the pulse generator circuit 70 provides internal circuitry to drive the indicator 32, and therefore, the driver 72 and/or current limiting resistor 74 are not present. Any type of switching apparatus 34 is anticipated, including providing a power disconnect by removal of one or more batteries 62.

In the metronome of FIG. 4, once the insulator 35 is extracted from between the contacts 37, power is supplied to the pulse generator circuit 70 and power pulses from the pulse generator circuit drive an audio transducer 84, typically, though not always required, through an audio amplification circuit or driver 82, as known in the industry. Any transducer 84 is anticipated including, but not limited to, a piezo-sounder, a relay, a buzzer, a speaker, etc.

Again, although flashing or sounding rates of 10 per minute and 100 per minute have been discussed, there is no limitation on the pulse rate from the generator circuit 70, and hence, the indicator 34 and/or audio transducer 84.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A manometer with a cadence indicator comprising:
    a housing;
    a gas pressure indicator;
    an input port on the housing for connecting to a source of gas pressure, such that the gas pressure at the input port is reflected in the gas pressure indicator, providing a pressure reading; and
    a cadence module interfaced to the housing such that cadence is provided concurrently from the local of the gas pressure indicator.

2. The manometer with a cadence indicator of claim 1, wherein the gas pressure indicator is a series of pressure indicia and a rotating pointer.

3. The manometer with a cadence indicator of claim 1, wherein the gas pressure indicator is a digital display.

4. The manometer with a cadence indicator of claim 1, wherein the cadence module emits light at a cadence pulse frequency.

5. The manometer with a cadence indicator of claim 4, wherein the cadence pulse frequency is 10 pulses per minute.

6. The manometer with a cadence indicator of claim 4, wherein the cadence pulse frequency is 100 pulses per minute.

7. The manometer with a cadence indicator of claim 1, wherein the cadence module emits sound at a cadence pulse frequency.

8. The manometer with a cadence indicator of claim 7, wherein the cadence pulse frequency is 10 pulses per minute.

9. A manometer with a cadence indicator comprising:
    a housing;
    a hub with pointer rotatably interfaced within the housing, the hub biased by a resilient member such that at atmospheric pressure, the pointer indicates a zero reading on a set of gas pressure indicia;
    an input port for connecting the manometer to a source of gas pressure, the input port providing the gas pressure to a diaphragm such that increases in the gas pressure above atmospheric pressure works against the bias of the resilient member, therefore rotating the hub such that the pointer addresses a corresponding indicia related to the pressure on the gas pressure indicia; and a cadence module interfaced to the housing such that cadence is provided concurrently from the local of the gas pressure indicia.

10. The manometer with a cadence indicator of claim 9, wherein the cadence module emits light at a cadence pulse frequency.

11. The manometer with a cadence indicator of claim 10, wherein the cadence pulse frequency is 10 pulses per minute.

12. The manometer with a cadence indicator of claim 10, wherein the cadence pulse frequency is 100 pulses per minute.

13. The manometer with a cadence indicator of claim 9, wherein the cadence module emits sound at a cadence pulse frequency.

14. The manometer with a cadence indicator of claim 13, wherein the cadence pulse frequency is 10 pulses per minute.

15. The manometer with a cadence indicator of claim 13, wherein the cadence pulse frequency is 100 pulses per minute.

* * * * *